United States Patent [19]

Brändström et al.

[11] Patent Number: 5,008,278

[45] Date of Patent: Apr. 16, 1991

[54] THERAPEUTICALLY ACTIVE COMPOUND AND A PROCESS FOR ITS PREPARATION

[75] Inventors: Arne E. Brändström, Göteborg; Per L. Lindberg, Askim; Gunnel E. Sunden, Göteborg, all of Sweden

[73] Assignee: Aktiebolaget Hassle, Molndal, Sweden

[21] Appl. No.: 454,047

[22] Filed: Dec. 20, 1989

[30] Foreign Application Priority Data

Dec. 22, 1988 [SE] Sweden .................... 8804629-7

[51] Int. Cl.$^5$ .................... A61K 31/445; C07D 213/06
[52] U.S. Cl. .................... 514/338; 546/271
[58] Field of Search .................... 514/338; 546/271

[56] References Cited

U.S. PATENT DOCUMENTS

| | | | |
|---|---|---|---|
| 4,182,766 | 1/1980 | Krasso | 546/271 |
| 4,255,431 | 3/1981 | Junggren | 546/271 |
| 4,337,257 | 6/1982 | Junggren | 424/263 |
| 4,359,465 | 11/1982 | Ruwant | 424/263 |
| 4,508,905 | 4/1985 | Junggren | 546/271 |
| 4,555,518 | 11/1985 | Rainer | 514/338 |
| 4,599,347 | 7/1986 | Krasso | 514/338 |
| 4,628,098 | 12/1986 | Nohara | 546/271 |
| 4,727,150 | 2/1988 | Nohara | 546/271 |
| 4,738,974 | 4/1988 | Brandstrom | 514/338 |
| 4,738,975 | 4/1988 | Nohara | 514/338 |

FOREIGN PATENT DOCUMENTS

| | | | |
|---|---|---|---|
| 0124495 | 11/1984 | European Pat. Off. | 546/271 |
| 176308 | 4/1986 | European Pat. Off. | 401/12 |
| 0208452 | 1/1987 | European Pat. Off. | 546/271 |
| 221041 | 5/1987 | European Pat. Off. | 401/12 |
| 0268956 | 6/1988 | European Pat. Off. | 401/12 |
| 279149 | 8/1988 | European Pat. Off. | 401/12 |
| 0295603 | 12/1988 | European Pat. Off. | 31/44 |
| 1500043 | 2/1975 | United Kingdom | 546/271 |
| 1525958 | 9/1978 | United Kingdom | 546/271 |

OTHER PUBLICATIONS

Derwent 87-294449/42 3/4/86.

Primary Examiner—Mary C. Lee
Assistant Examiner—Peter J. Davis
Attorney, Agent, or Firm—White & Case

[57] ABSTRACT

The novel compound 5-fluoro-2[[(4-cyclopropylmethoxy-2-pyridinyl) methyl]sulfinyl]-1H-benzimidazole and physiologically acceptable salts thereof as well as intermediates, pharmaceutical compositions containing the compound as active ingredient, and the use of the compound in medicine.

7 Claims, No Drawings

THERAPEUTICALLY ACTIVE COMPOUND AND A PROCESS FOR ITS PREPARATION

FIELD OF THE INVENTION

The object of the present invention is to provide a novel compound, and therapeutically acceptable salts thereof, which inhibit exogenously or endogenously stimulated gastric acid secretion and thus can be used in the prevention and treatment of peptic ulcer.

The present invention also relates to the use of the compound of the invention, especially therapeutically acceptable salts thereof, for inhibiting gastric acid secretion in mammals including man. In a more general sense, the compound of the invention may be used for prevention and treatment of gastrointestinal inflammatory diseases, and gastric acid-related diseases in mammals including man, such as gastritis, gastric ulcer, duodenal ulcer, reflux esophagitis, and Zollinger-Ellison syndrome. Furthermore, the compound may be used for treatment of other gastrointestinal disorders where gastric antisecretory effect is desirable e.g. in patients with gastrinomas, and in patients with acute upper gastrointestinal bleeding. It may also be used in patients in intensive care situations, and pre- and postoperatively to prevent acid aspiration and stress ulceration. The compound of the invention may also be used for treatment or prophylaxis of inflammatory conditions in mammals, including man, especially those involving lysozymal enzymes. Conditions that may be specifically mentioned are rheumatoid arthritis and gout. The compound may also be useful in the treatment of diseases related to bone metabolism disorders as well as the treatment of glaucoma. The invention also relates to pharmaceutical compositions containing the compound of the invention, or a therapeutically acceptable salt thereof, as active ingredient. In a further aspect, the invention relates to processes for preparation of such new compound, to novel intermediates in the preparation of the compound of the invention, and to the use of the active compound for the preparation of pharmaceutical compositions for the medical use indicated above.

It is a specific primary object of the invention to provide a compound with a high level of bioavailability. The compound of the invention will also exhibit high stability properties at neutral pH and a high potency in regard to inhibition of gastric acid secretion. Bioavailability is defined as the fraction, or percent, of the administered dose of compound that is absorbed unchanged into the systemic blood. Potency is in this application defined as the $ED_{50}$ value.

PRIOR ART AND BACKGROUND OF THE INVENTION

Benzimidazole derivatives intended for inhibiting gastric acid secretion are disclosed in numerous patent documents. Among these can be mentioned GB 1 500 043, GB 1 525 958, U.S. Pat. No. 4,182,766, U.S. Pat. No. 4,255,431, U.S. Pat. No. 4,599,347, EP 124 495, U.S. Pat. No. 4,555,518, U.S. Pat. No. 4,727,150, U.S. Pat. No. 4,628,098, EP 208 452 and Derwent abstract 87-294449/42. Benzimidazole derivatives proposed for use in the treatment or prevention of special gastrointestinal inflammatory diseases are disclosed in U.S. Pat. No. 4,539,465.

THE INVENTION

Compounds described in the prior art, as described above, are effective acid secretion inhibitors, and are thus useful as antiulcer compounds. In order to further enhance the usefulness of this type of drugs, a higher bioavailability has been desired, but still the compounds should have a high potency in inhibiting gastric acid secretion and also a high chemical stability at neutral pH.

It has been recognized that 2-[(2-pyridinylmethyl)-sulfinyl]-1H-benzimidazoles tested show a great variability in bioavailability as well as in potency and stability, and it is difficult to identify compounds possessing all the three advantageous properties. There is no guidance in the prior art on how to obtain compounds with this combination of properties.

It has been found that the compound of the invention shows exceedingly high bioavailability, and still the compound is very effective as inhibitor of gastric acid secretion and exhibits a high chemical stability in solution at a neutral pH. Thus the compound of the invention can be used in the indications given above in mammals including man.

The compound of the invention is 5-fluoro-2-[[(4-cyclo-propylmethoxy-2-pyridinyl)methyl]sulfinyl])-1H-benzimidazole (compound I) and physiologically acceptable salts thereof. The compound of the invention has an asymmetric centre in the sulfur atom, i.e. exists as two optical isomers (enantiomers). Both the pure enantiomers, racemic mixtures (50% of each enantiomer) and unequal mixtures of the two are within the scope of the present invention. Also five synthetic intermediates and process for the preparation are within the scope.

Preparation

The compound of the invention, may be prepared according to the following method:

Oxidizing 5-fluoro-2[[(4-cyclopropylmethoxy-2-pyridinyl)methyl]-thio-1H-benzimidazole (compound II) to give the compound of the invention. This oxidation may be carried out by using an oxidizing agent such as nitric acid, hydrogen peroxide, (optionally in the presence of vanadium compounds), peracids, peresters, ozone, dinitrogentetraoxide, iodosobenzene, N-halosuccinimide, 1-chlorobenzotriazole, t-butylhypochlorite, diazabicyclo[2,2,2]-octane bromine complex, sodium metaperiodate, selenium dioxide, manganese dioxide, chromic acid, cericammonium nitrate, bromine, chlorine, and sulfuryl chloride. The oxidation usually takes place in a solvent such as halogenated hydrocarbons, alcohols, ethers, ketones.

The oxidation may also be carried out enzymatically by using an oxidizing enzyme or microbiotically by using a suitable microorganism.

Depending on the process conditions and the starting materials, the compound of the invention is obtained either in neutral or salt form. Both the neutral compound and the salts of this are included within the scope of the invention. Thus, basic, neutral or mixed salts may be obtained as well as hemi, mono, sesqui or polyhydrates.

Alkaline salts of the compound of the invention are examplified by its salts with $Li^+$, $Na^+$, $K^+$, $Mg^{2+}$, $Ca^{2+}$, and $N^+(R)_4$, where R is (1-4 C)alkyl. Particularly preferred are the $Na^+$, $Ca^{2+}$ and $Mg^{2+}$ salts. Especially preferred are the $Na^+$ and $Mg^{2+}$ salts. Such salts may be prepared by reacting the compound with a base capable of releasing the desired cation.

Examples of bases capable of releasing such cations, and examples of reaction conditions are given below.

(a) Salts wherein the cation is $Li^+$, $Na^+$ or $K^+$ are prepared by treating the compound of the invention with LiOH, NaOH or KOH in an aqueous or nonaqueous medium or with LiOR, $LiNH_2$, $LiNR_2$, NaOR, $NaNH_2$, $NaNR_2$, KOR, $KNH_2$ or $KNR_2$, wherein R is an alkyl group containing 1–4 carbon atoms, in a nonaqueous medium.

(b) Salts wherein the cation is $Mg^{2+}$ or $Ca^{2+}$ are prepared by treating the compound of the invention with $Mg(OR)_2$ $Ca(OR)_2$ or $CaH_2$ wherein R is an alkyl group containing 1–4 carbon atoms, in a nonaqueous solvent such as an alcohol (only for the alcoholates), e.g. ROH, or in an ether such as tetrahydrofuran.

Racemates obtained can be separated into the pure enantiomers. This may be done according to known methods, e.g. from racemic diastereomeric salts by means of chromatography or fractional crystallization.

The starting materials described in the intermediate examples may be obtained according to processes known per se.

For clinical use the compound of the invention is formulated into pharmaceutical formulations for oral, rectal, parenteral or other modes of administration. The pharmaceutical formulation contains the compound of the invention normally in combination with a pharmaceutically acceptable carrier. The carrier may be in the form of a solid, semi-solid or liquid diluent, or a capsule. These pharmaceutical preparations are a further object of the invention. Usually the amount of active compound is between 0.1–95% by weight of the preparation, between 0.2–20% by weight in preparations for parenteral use and between 1–50% by weight in preparations for oral administration.

In the preparation of pharmaceutical formulations containing the compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, stabilizing substances such as alkaline compounds e.g. carbonates, hydroxides and oxides of sodium, potassium, calcium, magnesium and the like as well as with lubricating agents such as magnesium stearate, calcium stearate, sodium stearyl fumarate and polyethylenglycol waxes. The mixture is then processed into granules or pressed into tablets. Granules and tablets may be coated with an enteric coating which protects the active compound from acid catalyzed degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropyl-methylcellulose phthalate, partly methyl esterified methacrylic acid polymers and the like, if preferred in combination with a suitable plasticizer. To the coating various dyes may be added in order to distinguish among tablets or granules with different active compounds or with different amounts of the active compound present.

Soft gelatine capsules may be prepared with capsules containing a mixture of the active compound of the invention, vegetable oil, fat, or other suitable vehicle for soft gelatine capsules. Soft gelatine capsules may also be enteric-coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch, amylopectin, cellulose derivatives or gelatine. The hard gelatine capsules may be enteric-coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and/or polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use. Solutions for parenteral administration may be prepared as a solution of the compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance will depend on various factors such as for example the individual requirement of each patient, the route of administration and the disease. In general, oral and parenteral dosages will be in the range of 5 to 500 mg per day of active substance.

The invention is illustrated by the following examples.

Example 1 Preparation of 5-fluoro-2-[[(4-cyclopropylmethoxy-2-pyridinyl)methyl]sulfinyl]-1H-benzimidazole 5- Fluoro-2-[[(4-cyclopropylmethoxy-2-pyridinyl)-methyl]-thio]-1H-benzimidazole (1.25 g, 0.0036 mol) was dissolved in $CH_2Cl_2$ (40 ml). $NaHCO_3$ (0.6 g, 0.0072 mol) dissolved in $H_2O$ (20 ml) was added and the mixture was cooled to $+2°$ C. m-Chloroperbenzoic acid, 84% (0.73 g, 0.0036 mol) dissolved in $CH_2Cl_2$ (5 ml) was added under stirring. Stirring was continued at room temperature for 15 min. The two phases were separated and NaOH (0.29 g, 0.0072 mol) dissolved in $H_2O$ (25 ml) was added to the organic phase. The mixture was stirred, the phases were separated and the $H_2O$ phase was treated with Norite and filtered. Methylformiate (0.45 ml, 0.0073 mol) dissolved in $H_2O$ (5 ml) was added dropwise under stirring. After extraction with $CH_2Cl_2$ and drying with $Na_2SO_4$ the solvent was evaporated. In this way the title compound was obtained (0.93 g, 69%). NMR data for the final product is given below.

Example 2. Preparation of
5-fluoro-2-[[(4-cyclopropylmethoxy-2-pyridinyl)methyl]sulfinyl]-1H-bezimidazole, sodium salt 5-Fluoro-2-[[(4-cyclopropylmethoxy-2-pyridinyl)methyl]-sulfinyl]-1H-benzimidazole (5 g; 14.5 mmol) dissolved in dichloromethane (100 ml) and sodium hydroxide (0.56 g; 14 mmol) dissolved in water (100 ml) were transferred to a separatory funnel. The mixture was shaken to equilibrium whereupon the solvent phases were separated. The water solution was washed with dichloromethane (2×25 ml) and then freeze dried. The residue was recrystallized from dichloromethane/diethyl ether. Yield: 3.7 g (71%) of the title compound. NMR data is given below.

TABLE 1

| Ex. | Solvent | NMR data δ ppm (500 MHz) |
| --- | --- | --- |
| 1. | CDCl$_3$ | 0.22 (m, 2H); 0.60 (m, 2H); 1.10 (m, 1H); 3.45 (m, 1H); 3.60 (m, 1H); 4.52 (d, 1H); 4.70 (d, 1H); 6.65 (d, 1H); 6.70 (dd, 1H); 7.08 (m, 1H); 7.30–7.90 (b, 2H); 8.28 (d, 1H) |
| 2. | D$_2$O δ(D$_2$O, 4.82) | 0.09 (m, 2H); 0.49 (m, 2H); 0.88 (m, 1H); 2.92 (m, 1H); 3.34 (m, 1H); 4.62 (d, 1H); 4.71 (d, 1H); 6.05 (d, 1H); 6.75 (m, 1H); 7.05 (m, 1H); 7.33 (m, 1H); 7.58 (m, 1H); 8.23 (d, 1H) |

Preparation of synthetic intermediates

Example I 1. Preparation of
4-cyclopropylmethoxy-2-methylpyridine-1-oxide.

To sodium hydride (55% pure) (4.4 g, 0.1 mol) (washed with petroleum ether), cyclopropyl-methanol (50 ml) was added. Then a solution of 2-methyl-4-nitropyridine-N-oxide (6.5 g, 0.042 mol) in cyclopropylmethanol (30 ml) was added during about 1 h. The dark brown mixture was heated to 90° C. and stirred at 90° C. for about 1 h. Thereafter the cyclopropylmethanol was distilled off under reduced pressure and methylene chloride (100 ml) was added to the residue. The mixture was stirred for about 30 minutes, then filtered and concentrated which gave 9.5 g of crude material.

The crude material was purified by flash chromatography on silica with methylene chloride-methanol (90–10) as eluent, giving 4.0 g (53%) of pure title compound. NMR data is given below.

Example I 2. Preparation of
2-acetoxymethyl-4-cyclo-propylmethoxypyridine.

4-cyclopropylmethoxy-2-methylpyridine-1-oxide (3.8 g 0.021 mol) was dissolved in acetic anhydride (10 ml) and was added dropwise to acetic anhydride (20 ml) (warmed to 90° C.). After the addition the temperature was raised to 110° C. and the mixture was stirred at 110° C. for 1 h and then the solvent was distilled off and the crude product was used without purification. NMR data is given below.

Example I 3. Preparation of
4-cyclopropylmethoxy-2-hydroxymethylpyridine

To the crude 2-acetoxymethyl-4-cyclopropylmethoxy pyridine, NaOH (100 ml 2M) was added and the mixture was refluxed for 2 hours. The mixture was extracted with methylene chloride, and the phases were separated. The organic layer was dried with Na$_2$SO$_4$, filtered and the solvent was evaporated off, yielding 2.7 g of crude title compound. NMR data is given below. The crude product was used without any further purification.

Example I 4. Preparation of
4-cyclopropylmethoxy-2-chloromethylpyridine hydrochloride 4-cyclopropylmethoxy-2-hydroxymethyl pyridine (93% pure) (0.9 g 0.0046 mol) was dissolved in methylene chloride (10 ml) and cooled to 0° C. SOCl$_2$ (0.5 ml, 0.0069 mol) in methylene chloride (5 ml) was added dropwise at 0° C. and the reaction mixture was stirred 15 min at room temperature. Isopropanol (0.5 ml) was added and the mixture was evaporated giving the desired product (0.68 g, 78%). NMR-data is given below.

Example I 5. Preparation of
5-fluoro-2-[[(4-cyclopropylmethoxy-2-pyridinyl)methyl)thio]-1H-benzimidazole used as starting material To 5-fluoro-2-mercapto-1H-benzimidazole (0.88 g, 0.0051 mol) in methanol (25 ml) NaOH (0.2 g, 0.0051 mol) dissolved in H$_2$O (1 ml) and 4-cyclopropylmethoxy-2-chloromethyl-pyridine hydrochloride (0.91 g, 0.0046 mol) dissolved in methanol (10 ml) were added in the given order. The mixture was heated to boiling and NaOH (0.2 g, 0.005 mol) dissolved in H$_2$O (1 ml) was added and the mixture was refluxed for 1 hour. After evaporation of methanol, CH$_2$Cl$_2$ (75 ml) and H$_2$O (50 ml) were added and pH adjusted to 10. The mixture was vigorously stirred, the phases were separated, the organic phase was dried over Na$_2$SO$_4$ and evaporated giving the desired product (1.25 g, 72%). NMR data for the product is given below.

TABLE 2

| Ex | Solvent | NMR data δ ppm |
| --- | --- | --- |
| I 1. | CDCl$_3$ (500 MHz) | 0.36 (m, 2H); 0.68 (m, 2H); 1.26 (m, 1H); 2.52 (s, 3H); 3.83 (d, 2H); 6.70 (dd, 1H); 6.77 (d, 1H); 8.16 (d, 1H) |
| I 2. | CDCl$_3$ (500 MHz) | 0.37 (m, 2H); 0.69 (m, 2H); 2.16 (s, 3H); 3.87 (d, 2H); 6.75 (dd, 1H); 6.87 (d, 1H); 8.42 (d, 1H) |
| I 3. | CDCl$_3$ (500 MHz) | 0.36 (m, 2H); 0.67 (m, 2H); 1.27 (m, 1H); 3.86 (d, 2H); 4.69 (s, 2H); 6.72 (dd, 1H), 6.78 (d, 1H); 8.33 (d, 1H) |
| I 4. | DMSO-d$_6$ (300 MHz) | 0.40 (m, 2H); 0.60 (m, 2H), 1.30 (m, 1H); 4.20 (d, 2H); 5.00 (s, 2H); 7.45 (dd, 1H); 7.65 (d, 1H); 8.70 (d, 1H) |
| I 5. | CDCl$_3$ (500 MHz) | 0.36–0.39 (m, 2H); 0.67–0.71 (m, 2H); 1.27 (m, 1H); 3.89 (d, 2H), 4.29 (s, 2H); 6.81 (dd, 1H); 6.89 (d, 1H); 6.94 (m, 1H); 7.24 (dd, 1H); 7.46 (dd, 1H), 8.43 (d, 1H) |

The best mode of carrying out the invention known at present is to use the sodium salt of the compound of the invention, thus the compound described in Example 2. Pharmaceutical preparations containing the compound of the invention as active ingredient are illustrated in the following formulations.

Syrup
A syrup containing 1% (weight per volume) of active substance was prepared from the following ingredients:

Compound according to Example 1      1.0 g

-continued

Syrup

A syrup containing 1% (weight per volume) of active substance was prepared from the following ingredients:

| Sugar, powder | 30.0 g |
|---|---|
| Saccharine | 0.6 g |
| Glycerol | 5.0 g |
| Flavouring agent | 0.05 g |
| Ethanol 96% | 5.0 g |
| Distilled water q.s. to a final volume of | 100 ml |

Sugar and saccharine were dissolved in 60 g of warm water. After cooling the active compound was added to the sugar solution and glycerol and a solution of flavouring agents dissolved in ethanol were added. The mixture was diluted with water to a final volume of 100 ml.

Enteric-coated tablets

An enteric coated tablet containing 50 mg of active compound was prepared from the following ingredients:

| I | Compound according to Example 1 as Mg salt | 500 g |
|---|---|---|
| | Lactose | 700 g |
| | Methyl cellulose | 6 g |
| | Polyvinylpyrrolidone cross-linked | 50 g |
| | Magnesium stearate | 15 g |
| | Sodium carbonate | 6 g |
| | Distilled water | q.s. |
| II | Cellulose acetate phthalate | 200 g |
| | Cetyl alcohol | 15 g |
| | Isopropanol | 2000 g |
| | Methylene chloride | 2000 g |

I Compound according to example 1, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 50 mg of active substance, in a tabletting machine using 7 mm diameter punches.

II A solution of cellulose acetate phthalate and cetyl alcohol in isopropanol/methylene chloride was sprayed onto the tablets I in an Accela Cota ®, Manesty coating equipment. A final tablet weight of 110 mg was obtained.

Solution for intravenous administration

A parenteral formulation for intravenous use, containing 4 mg of active compound per ml, was prepared from the following ingredients:

| Compound according to Example 2 | 4 g |
|---|---|
| Sterile water to a final volume of | 1000 ml |

The active compound was dissolved in water to a final volume of 1000 ml. The solution was filtered through a 0.22 μm filter and immediately dispensed into 10 ml sterile ampoules. The ampoules were sealed.

Capsules

Capsules containing 30 mg of active compound were prepared from the following ingredients:

| Compound according to Example 1 | 300 g |
|---|---|
| Lactose | 700 g |
| Microcrystalline cellulose | 40 g |
| Hydroxypropyl cellulose low-substituted | 62 g |
| Disodium hydrogen phosphate | 2 g |
| Purified water | q.s. |

The active compound was mixed with the dry ingredients and granulated with a solution of disodium hydrogen phosphate. The wet mass was forced through an extruder and spheronized and dried in a fluidized bed dryer.

500 g of the pellets above were first coated with a solution of hydroxypropyl methylcellulose, 30 g, in water, 750 g, using a fluidized bed coater. After drying, the pellets were coated with a second coating as given below:

| Coating solution: | |
|---|---|
| Hydroxypropyl methylcellulose phthalate | 70 g |
| Cetyl alcohol | 4 g |
| Acetone | 200 g |
| Ethanol | 600 g |

The final coated pellets were filled into capsules.

Suppositories

Suppositories were prepared from the following ingredients using a welding procedure. Each suppository contained 40 mg of active compound.

| Compound according to Example 1 | 4 g |
|---|---|
| Witepsol H-15 | 180 g |

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

BIOLOGICAL EFFECTS

Bioavailability

Choice of Species for Testing

The results from tests on two different animal species, rat and dog, vary in regard to measured level of bioavailability for the same compound. We believe that the rat is the more relevant species for bioavailability testing. This is based on our belief that liver metabolism has the most predominant impact upon bioavailability, and that the liver metabolic pattern in man for this type of compounds is quite similar to that of the male rat (more so than of the female rat and the dog). Moreover, test results of bioavailability in the male rat will tend to give a broader "spread" compared with the test results in the dog, and thus the male rat model will give more clear differences in bioavailability between different compounds. Stated in another way, the bioavailability as tested in the male rat can be expected to give a better estimate of the relative differences in man between different test compounds compared with the test results obtained when using the same compounds in the dog.

Assessment of Bioavailability

Bioavailability is assessed by calculating the quotient between the area under plasma concentration (AUC) curve following intraduodenal (id) administration and intravenous (iv) administration from the rat or the dog. Low, therapeutically relevant doses, were used. This method is scientifically recognized as valid for assessing bioavailability (see for instance: M. Rowland and T. N. Tozer, Clinical Pharmacokinetics, 2nd ed., Lea & Febiger, London 1989, p 42). The data from both the rat and the dog are provided in Table 3.

Rough Screening Model

Since the bioavailability model described above is time and labour intensive, and requires a large number of plasma analyses, also a rough screening model, based on relative potencies to inhibit acid secretion, has been used (see for instance: A. Goth, Medical Pharmacology, 7th ed., C. V. Mosby Company, Saint Louis 1974, p 19). Thus, the ratio (called "Bioavailability" in Table 3) between the $ED_{50}$ at intravenous administration and the $ED_{50}$ at intraduodenal administration was calculated. Also these data are provided in Table 3.

Potency

The potency for inhibition of acid secretion has been measured in the male rat and the dog, both intravenously and intraduodenally. When it comes to relevance of the animal test data for potency of a given compound in man for the present type of compounds, it is believed that potency in man will correspond to a level somewhere between what is measured in the male rat and what is measured in the dog. Potency data from the two animal species are given in Table 3.

Biological Tests

Inhibition of Gastric Acid Secretion in the Conscious Male Rat.

Male rats of the Sprague-Dawley strain were used. They were equipped with cannulated fistulae in the stomach (lumen) and the upper part of the duodenum, for collection of gastric secretions and administration of test substances, respectively. A fourteen days recovery period after surgery was allowed before testing commenced.

Before secretory tests, the animals were deprived of food but not water for 20 h. The stomach was repeatedly washed through the gastric cannula, and 6 ml of Ringer-Glucose given s.c. Acid secretion was stimulated with a infusion during 3.5 h (1.2 ml/h, s.c.) of pentagastrin and carbachol (20 and 110 nmol/kg h, respectively), during which time gastric secretions were collected in 30-min fractions. Test substances or vehicle were given iv or id at 90 min after starting the stimulation, in a volume of 1 ml/kg. Gastric juice samples were titrated to pH 7.0 with NaOH, 0.1 mol/L, and acid output calculated as the product of titrant volume and concentration. Further calculations were based on group mean responses from 4–5 rats. The acid output during the periods after administration of test substances or vehicle were expressed as fractional responses, setting the acid output in the 30-min period preceding administration to 1.0. Percentage inhibition was calculated from the fractional responses elicited by test compound and vehicle. $ED_{50}$-values were obtained from graphical interpolation on log dose-response curves, or estimated from single-dose experiments assuming a similar slope for all dose-response curves. An estimation of the bioavailability was obtained by calculating the ratio $ED_{50}iv/ED_{50}id$. The results reported are based on gastric acid secretion during the second hour after drug/vehicle administration.

Bioavailability in the Male Rat

Male adult rats of the Sprague-Dawley strain were used. One day, prior to the experiments, all rats were prepared by cannulation of the left carotid artery under anaesthesia. The rats used for the intravenous experiments, were also cannulated in the jugular vein. (Ref. V Popovic and P Popovic, J Appl Physiol 1960;15,727–728). The rats used for the intraduodenal experiments, were also cannulated in the upper part of the duodenum. The cannulas were exteriorized at the nape of the neck. The rats were housed individually after surgery and were deprived of food, but not water, before administration of the test substances. The same dose (4 μmol/kg) were given iv and id as a bolus for about one minute (2 ml/kg).

Blood samples (0.1–0.4 g) were drawn repeatedly from the carotid artery at interval-s up to 4 hours after given dose. The samples were frozen as soon as possible until analysis of the test compound.

The area under the blood concentration vs time curve, AUC, was determined by the linear trapezoidal rule and extrapolated to infinity by dividing the last determined blood concentration by the elimination rate constant in the terminal phase. The systemic bioavailability (F %) following intraduodenal administration was calculated as $$F(\%) = \frac{AUC_{id}}{AUC_{iv}} \times 100$$

Inhibition of Gastric Acid Secretion and Bioavailability in the Conscious Dog.

Harrier dogs of either sex were used. They were equipped with a duodenal fistula for the administration of test compounds or vehicle and a cannulated ventricular fistula for the collection of gastric secretions.

Before secretory tests the animals were fasted for about 18 h but water was freely allowed. Gastric acid secretion was stimulated by a 4 h infusion of histamine dihydrochloride (12 ml/h) at a dose producing about 80% of the individual maximal secretory response, and gastric juice collected in consecutive 30-min fractions. Test substance or vehicle was given id or iv 1 h after starting the histamine infusion, in a volume of 0.5 ml/kg body weight. The acidity of the gastric juice samples were determined by titration to pH 7.0, and the acid output calculated. The acid output in the collection periods after administration of test substance or vehicle were expressed as fractional responses, setting the acid output in the fraction preceding administration to 1.0. Percentage inhibition was calculated from fractional responses elicited by test compound and vehicle. $ED_{50}$-values were obtained by graphical interpolation on log dose–response curves, or estimated from single-dose experiments under the assumption of the same slope of the dose-response curve for all test compounds. All results reported are based on acid output 2 h after dosing.

Blood samples for the analysis of test compound concentration in plasma were taken at intervals up to 3 h after dosing. Plasma was separated and frozen within 30 min after collection. AUC (area under the plasma concentration—time curve), extrapolated to infinite time, was calculated by the linear trapezoidal rule. The systemic bioavailability (F %) after id administration was calculated as $100 \times (AUC_{id}/AUC_{iv})$.

Chemical Stability

The chemical stability of various compounds of the invention has been followed kinetically at low concentration at 37° C. in aqueous buffer solution at different pH values. The results in Table 3 show the half life (t ½) at pH 7, that is the time period after which half the amount of the original compound remains unchanged.

Results of biological and stability tests

Table 3 gives a summary of the test data available for the compound of the invention and a structurally closely related compound in the prior art, called Ref. in Table 3, namely 5-fluoro-2-[[(4-isopropoxy-2-pyridinyl)-methyl]sulfinyl]-1H-benzimidazole described in U.S. Pat. No. 4,727,150. As can be seen from Table 3 the compound according to the invention has a high bioavailability (F= 82% in the rat), high potency ($ED_{50}iv = 1.2$ μmol/kg, $ED_{50}id = 2.2$ μmol/kg in the rat) and a high chemical stability (t ½ = 23 h). Moreover, considering the most distinguishing property for the compound of the invention, the bioavailability, the compound of the invention has a much higher value (82% vs 31%) compared to that of the Ref. compound, and is better in the other properties as well ($ED_{50}iv = 1.8$ μmol/kg, $ED_{50}id = 4.0$ μmol/kg and t ½ = 14 h for the Ref compound).

TABLE 3

Biological Test Data and Stability Data

| Test compound Example no. | Inhibition of acid secretion | | | | "Bioavailability" measured by the Rough Screening Model Rat $ED_{50}iv$/ $ED_{50}id$ (%) | Bioavailability measured by the AUC-method F% | | Chemical stability at pH 7 half-life (t ½) h |
|---|---|---|---|---|---|---|---|---|
| | Dog $ED_{50}$ (μmol/kg) Route of adm. | | Rat, $ED_{50}$ (μmol/kg) Route of adm. | | | | | |
| | iv | id | iv | id | | Dog | Rat | |
| 1 | (1) | 1.0 | 1.2 | 2.2 | 55 | 80 | 82 | 23 |
| Ref. | n.t. | (2) | 1.8 | 4.0 | 45 | n.t. | 31 | 14 | n.t. = not tested
(1) Dog 1 1 μmol/kg gave 35% inhibition
Dog 2 1 μmol/kg gave no effect
Dog 3 2 μmol/kg gave 98% inhibition.
Thus no $ED_{50}$ value could be estimated.
(2) Dog 4 3 μmol/kg gave 95% inhibition
Dog 5 3 μmol/kg gave 98% inhibition
Thus no $ED_{50}$ value could be estimated.

We claim:

1. 5-Fluoro-2[[(4-cyclopropylmethoxy-2-pyridinyl)-methyl]sulfinyl]-1H-benzimidazole or physiologically acceptable salts thereof, or its optical enantiomers.

2. The sodium salt of the compound according to claim 1.

3. The magnesium salt of the compound according to claim 1.

4. A pharmaceutical composition containing as active ingredient an effective amount of the compound according to claim 1.

5. A method for inhibiting gastric acid secretion by administering to mammals an amount of a compound as defined in claim 1 sufficient to inhibit gastric acid secretion.

6. A method for the treatment of gastrointestinal inflammatory diseases in mammals by administering an amount of a compound as defined in claim 1 sufficient for the treatment of gastrointestinal inflammatory diseases.

7. 5-fluoro-2-[[(4-cyclopropylmethoxy-2-pyridinyl)-methyl]-thio]-1H-benzimidazole.

* * * * *

UNITED STATES PATENT AND TRADEMARK OFFICE
CERTIFICATE OF CORRECTION

PATENT NO. : 5,008,278       Page 1 of 2
DATED : April 16, 1991
INVENTOR(S) : Arne E. Brandstrom; Per L. Lindberg;
Gunnel E. Sunden It is certified that error appears in the above-identified patent and that said Letters Patent is hereby corrected as shown below:

Cover page, item [54], and col. 1, line 1,
"THERAPEUTICALLY ACTIVE COMPOUND AND A PROCESS FOR ITS PREPARATION" should read --THERAPEUTICALLY ACTIVE CYCLOPROPYL SUBSTITUTED COMPOUND--;

col. 2, line 29, after "the invention" insert
--having the formula,

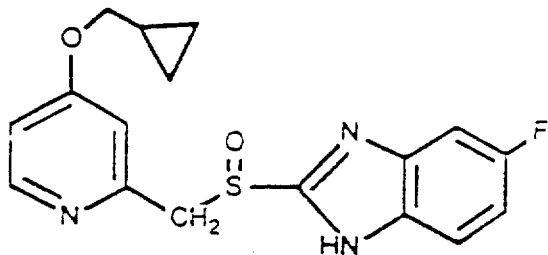

UNITED STATES PATENT AND TRADEMARK OFFICE
CERTIFICATE OF CORRECTION

PATENT NO. : 5,008,278

DATED : April 16, ±991

INVENTOR(S) : Arne E. Brandstrom, et al

It is certified that error appears in the above-identified patent and that said Letters Patent is hereby corrected as shown below:

Col. 10, line 25. "interval-s" should read --intervals--:

Signed and Sealed this

Sixteenth Day of February, 1993

Attest:

STEPHEN G. KUNIN

Attesting Officer

Acting Commissioner of Patents and Trademarks